United States Patent [19]

Greco et al.

[11] Patent Number: 5,783,730
[45] Date of Patent: Jul. 21, 1998

[54] FORMATION OF STYRENE PHOSPHONIC ACID

[75] Inventors: Carl C. Greco, Garnerville; John Tomko, Dobbs Ferry, both of N.Y.

[73] Assignee: Akzo Nobel NV, Arnhem, Netherlands

[21] Appl. No.: 850,312

[22] Filed: May 2, 1997

[51] Int. Cl.$^6$ ............................................. C07F 9/38
[52] U.S. Cl. ............................................. 562/8
[58] Field of Search ................................. 562/8

[56] References Cited

U.S. PATENT DOCUMENTS

| | | | |
|---|---|---|---|
| 2,694,684 | 11/1954 | Rogers et al. | 252/49.8 |
| 3,501,556 | 3/1970 | Weil et al. | 260/953 |
| 4,486,357 | 12/1984 | Krause . | |
| 4,507,249 | 3/1985 | Pieper et al. | 260/502.4 R |
| 5,132,444 | 7/1992 | Northemann et al. | 558/83 |
| 5,391,816 | 2/1995 | Tomko | 562/8 |

FOREIGN PATENT DOCUMENTS

WO 96/24599  8/1996  WIPO ................. C07F 9/38

OTHER PUBLICATIONS

CA:103:37610 abs of DE3323392, Jan. 1985.

*Primary Examiner*—Alan L. Rotman
*Assistant Examiner*—Jean F. Vollano
*Attorney, Agent, or Firm*—Richard P. Fennelly; Louis A. Morris

[57] ABSTRACT

Styrene phosphonic acid (SPA) can be formed the reaction of phosphorous acid with acetophenone, preferably in the presence of a Lewis acid catalyst, to form a hydroxy adduct intermediate thereof which is then reacted with acetic anhydride to form the acyl derivative of the hydroxy adduct, followed by removal of an acetic acid moiety therefrom, preferably in the presence of an acidic catalyst, to form the styrene phosphonic acid product.

7 Claims, 1 Drawing Sheet

FORMATION OF STYRENE PHOSPHONIC ACID

BACKGROUND OF THE INVENTION

Styrene phosphonic acid (SPA) has traditionally been formed from phosphorus trichloride, water and acetophenone. In this type of reaction, however, the isolatable yields of SPA have been low and there are many undesired by-products. In addition, this reaction route necessitates the careful addition of water to the reactants to reduce foaming problems and excess heat formation. When phosphorus trichloride reacts with water there is also the formation of hydrogen chloride which needs to be removed from the reaction medium by either vacuum or nitrogen purge thereby increasing the manufacturing cost for SPA.

SUMMARY OF THE INVENTION

Styrene phosphonic acid (SPA) is formed by the process of the present invention by the reaction of phosphorous acid with acetophenone, preferably in the presence of a Lewis acid catalyst, to form a hydroxy adduct intermediate thereof which is then reacted with acetic anhydride to form the acyl derivative of the hydroxy adduct, followed by removal of an acetic acid moiety therefrom, preferably in the presence of an acidic catalyst, to form the styrene phosphonic acid product.

Styrene phosphonic acid is currently used in a number of end use applications. It can be used in the dispersion of aluminum flakes in water-borne paints and as a primer for aerospace coatings. It may also find use in epoxy coatings, in photolithography applications, and as a multifunctional additive for polybutadiene-polystyrene copolymers.

DESCRIPTION OF THE DRAWING

The Drawing, FIG. 1, which forms a portion of the present specification, illustrates a particularly preferred flow diagram illustrating practice of the present invention.

DESCRIPTION OF THE PREFERRED EMBODIMENTS

Figure 1:
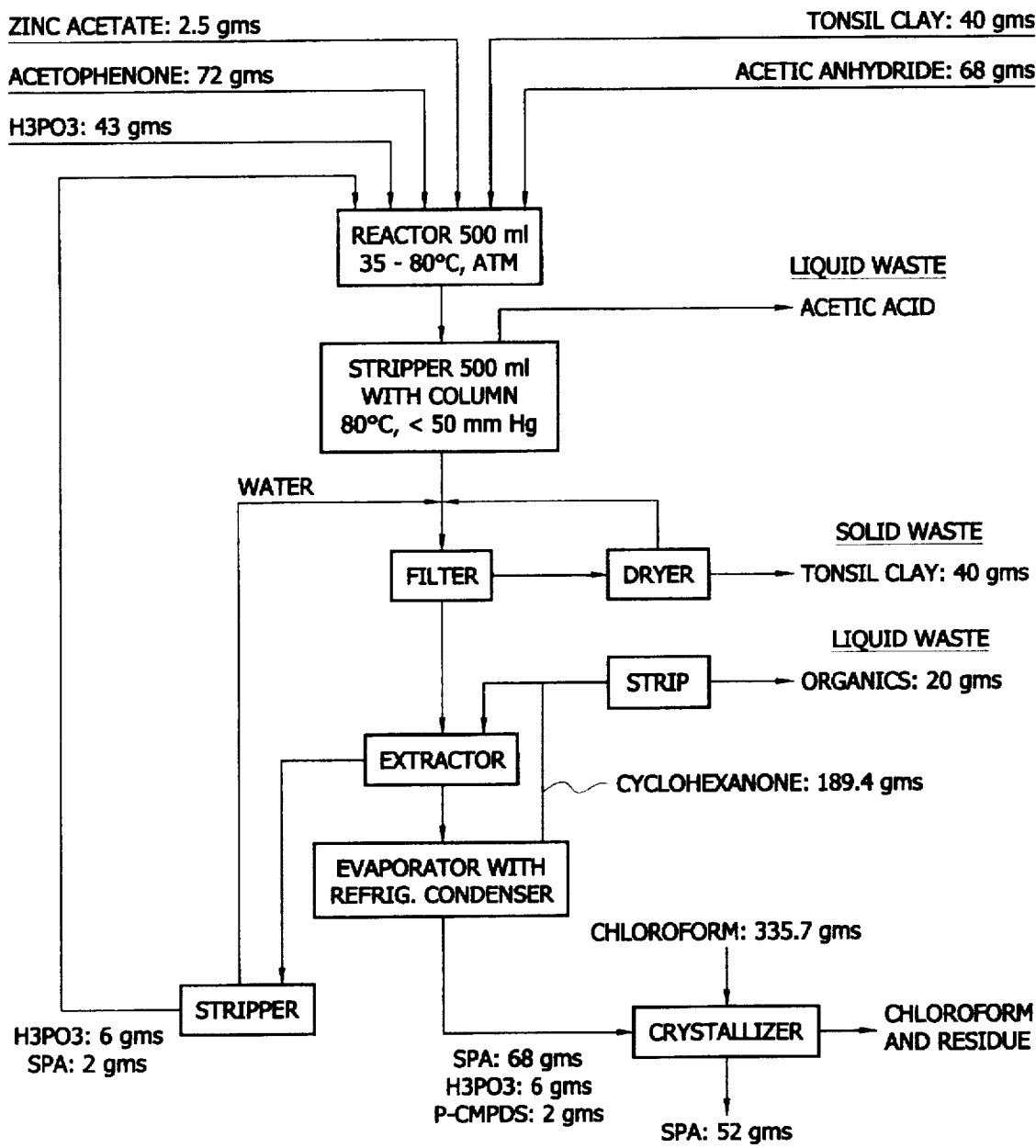

The initial step in the process of the claimed invention is the reaction of stoichiometric amounts phosphorous acid and acetophenone, preferably in the presence of a Lewis acid catalyst, to form a hydroxy adduct intermediate thereof which has the formula

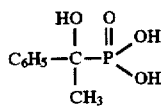

Representative Lewis acid catalysts which can be used are well known to persons of ordinary skill in the art. Representative catalysts for use include the chlorides and acetates of such metals as zinc and aluminum, as well as acidic zeolitic materials. The amount which is employed is a catalytic amount (e.g., up to about 3%, by weight of the reagents, for example, from about 1% to about 3%, by weight of the regents) and the reaction temperature will generally be in the range of from about 25° C. to about 55° C. The reaction may be either be carried out without or with a suitable organic solvent reaction medium, such as acetic acid or tetrahydrofuran.

Thereafter, as the second major step of the instant process, the above-depicted hydroxy adduct intermediate thereof which is then reacted, in an exothermic manner, with acetic anhydride to form the acyl derivative of the hydroxy adduct which has the formula

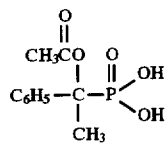

During this step in the reaction, the reaction temperature will likely rise about from about 25° C. to about 55° C.

The acyl derivative of the hydroxy adduct that was previously described is then treated in a deacylation step with an acidic catalyst to remove an acetic acid moiety therefrom to yield the desired SPA endproduct which has the formula

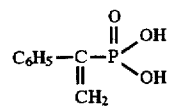

The type of acid catalyst which is preferred for use in this one which is an "immobilized" acid catalyst in that the acid moieties are contained on a support or matrix which can be easily filtered and removed from the final reaction mixture. Acidic clays or acidic ion exchange resins are examples of suitable catalysts of this type to use. The reaction temperature during this step of the process will generally be in the range of from about 70° C. to about 100° C.

The SPA product will be in the organic layer resulting from the previously described process sequence and can be recovered by filtering off the acidic clay or resin, for example, and recovering the desired SPA product by stripping off the organic solvent in which it is contained. The by-product, unreacted phosphorous acid can be removed by washing the organic solution with water. If desired, the purity of the recovered SPA product can be improved, if necessary, by appropriate recrystallization from a suitable solvent, such as chloroform.

The present invention is further understood by reference to the Examples which follow.

EXAMPLE 1

Into a 250 ml flask, equipped with a stirrer, thermometer and dropping funnel, was added 38 gm (0.3 mole) of acetophenone, 24.5 gm (0.3 mole) of phosphorous acid, and 1.5 gm of zinc chloride. The flask was continuously purged with nitrogen, and its contents were heated to 60° C. The reaction mixture was held at this temperature for one hour and then 36 gm of acetic anhydride was added at a temperature between 40° C. and 60° C. over a twenty minute period. After the addition, the reaction mixture was heated for two hours at 60° C. Then, 15 gm of AMBERLYST 36 brand ion exchange resin was added to the reaction mixture, and the resulting slurry was distilled at 80° C. and a vacuum of 20 mm mercury. After two hours of distillation at this temperature and pressure, no more distillate was produced, and the distillation was stopped. A residue (70 gm) remained in the flask, and it was filtered to remove the ion exchange resin to yield a final product having a weight of 55 gm (theoretical yield: 56.1 gm). The residue was analyzed using phosphorus NMR and was shown to contain three phosphorus-containing compounds. By calculating the weight percentages of these three compounds, it was determined that the product contained 75 wt % styrene phosphonic acid (SPA), 23 wt % unreacted phosphorous acid, and 2 wt % Diels-Alder dimer phosphorus compound. The yield of SPA from this analysis, based on unreacted phosphorous acid, was therefore 62%.

EXAMPLE 2

The same procedure that was employed in Example 1 was used without any catalyst being employed. It was determined that the product contained 48 wt % styrene phosphonic acid (SPA), 40 wt % unreacted phosphorous acid, and 12 wt % other phosphorus compounds. The yield of SPA in this reaction was therefore only 36%.

EXAMPLE 3

The same procedure that was employed in Example 1 was used with aluminum chloride being used as the catalyst. The distillation was performed without the ion exchange resin, and a heating temperature of 120° C. was needed to remove the acetic acid in the formation of the desired SPA product. It was determined that the product contained 62 wt % styrene phosphonic acid (SPA), 22 wt % unreacted phosphorous acid, and 16 wt % Diels-Alder dimer phosphorus compound. The yield of SPA in this reaction was therefore 50%.

EXAMPLE 4

The same procedure that was employed in Example 1 was used with zinc acetate being used as the catalyst instead of zinc chloride. It was determined that the product contained 80 wt % styrene phosphonic acid (SPA), 18 wt % unreacted phosphorous acid, and 2 wt % Diels-Alder dimer phosphorus compound. The yield of SPA in this reaction was therefore 67% of theory.

EXAMPLE 5

In this Example, an acid catalyst (ZSM-5-40 zeolite) was used for both the reaction of phosphorous acid (24.6 gm) with 36 gm of acetophenone (at 75° C.) and the subsequent reaction (at 80° C.) to crack the acyl derivative to form SPA. The amount of catalyst used in the first reaction was 12 gm. It was determined that the product contained 77 wt % styrene phosphonic acid (SPA), 17 wt % unreacted phosphorous acid, and 6 wt % Diels-Alder dimer phosphorus compound. The yield of SPA in this reaction was therefore 65% of theory.

EXAMPLE 6

This Example illustrates a particularly preferred process for practice of the present invention and is depicted in the Drawing which forms a part of the present specification.

As a general description, the phosphorous acid was first mixed with a stoichiometric amount of acetophenone and a catalytic amount of zinc acetate in a three-neck flask which was equipped with a stirrer, condenser and a dropping funnel. The reaction mixture was then heated to 35° C. with vigorous stirring. At this temperature, the acetic anhydride was then added dropwise over a thirty minute period, producing an exothermic reaction during which the temperature rose to around 50° C. The reaction mixture was held at this temperature for four hours by heating with a constant temperature oil bath.

A nitrogen flow was started going through the flask and condenser. The flask was flushed out and a positive flow of nitrogen was continued to be maintain through the system.

Then, 147 gm. of phosphorous acid and 216 gm of acetophenone were added to the flask, followed by the addition of 7.5 gm of zinc acetate catalyst. Stirring was started under nitrogen for one hour at 25° C., and then 204 gm of acetic anhydride was added, dropwise, over a thirty to sixty minute period. The addition was exothermic and the temperature rose to about 50° C.

After the previous additions were made, the reaction mixture was heated with an oil bath at 45° C. to 50° C. for at least a four hour duration. The reaction mixture was then cooled to room temperature and 60 gm of the dry tonsil supreme clay was added. The resulting slurry was vigorously stirred and was heated at 100° C. for three hours.

After the heating period, the entire reaction mixture was set up for distillation in the same reaction flask after being equipped with a distillation head. The heating temperature was keep around 100° C. and the vacuum about 10 mm of Hg.

After about two hours, the acetic acid and unreacted acetic anhydride had been removed, and the distillation residue was treated with 500 ml of water, was stirred for thirty minutes and was then filtered through a Buchner funnel with the desired SPA product dissolving in the water. The filtered material was washed with 100 ml of water. The washings were then added to the flask containing the filtrate. The clay was sucked dry and discarded. The filtrate was extracted with 600 ml of cyclohexanone in a 2000 ml flask with a bottom stopcock, with stirring for fifteen to twenty minutes. The bottom layer, which was the organic phase, contained the desired SPA product and was separated from the aqueous layer and was stripped on a flash evaporator. An amber-brown solid remained as the crude product in 235 gm quantity. Analysis by P-NMR showed that the product contained 90% SPA, 8% $H_3PO_3$, and 2% of another phosphorus compound. The yield of isolated SPA in this reaction was 64% of theory.

The distillate from the organic extract was analyzed by GLC and was found to contain 60 gm of acetophenone dissolved in the cyclohexanone. The aqueous solution from the extraction step was stripped to constant weight (31 gm.) and was found by NMR to contain 30 gm of $H_3PO_3$ and 1.0 gm of SPA. This residue sample was used in another experiment.

The following illustrates a second reaction in accordance with the present invention with a first recycle of phosphorous acid.

In this procedure 31 gm of the SPA product from the procedure described above, was mixed with 117 gm of fresh phosphorous acid, 216 gm of acetophenone, 7.5 gm of zinc acetate, and 204 gm of acetic anhydride. The same procedure was used as previously described and was found to produce about the same yield of SPA.

The following illustrates the crystallization of the crude reaction product from above procedures. Into a 500 ml Erlenmeyer flask was placed 50 gm of the crude 71 gm SPA product obtained from the first reaction procedure. To this was added then 160 ml of chloroform at room temperature. The resulting slurry was heated to 65° C.–70° C. with constant stirring. At this temperature, the solids went into solution, and the chloroform started to boil. The flask was removed from the heat and was placed on a magnetic stirring plate to cool with constant stirring. When the temperature reached 30° C. in about one hour, a few crystals of SPA were added to the clear solution. The flask was continued to be cooled to about 15° C. at which time the flask with the SPA-chloroform solution was transferred to a refrigerator (held at 4° C.). The crystallizing mixture was allowed to sit in the refrigerator overnight. The next day, the reaction mixture was filtered using a course Buchner funnel. The product on the funnel was sucked dry, without washing with any solvent. The crystallized SPA product was air-dried and weighed, 32 gm or 64% yield). The filtrate was placed in a one neck flask and was stripped to constant weight. A viscous brown oil remained in 18 gm quantity. This residue was dissolved in 40 ml of fresh chloroform, was heated to 65° C. and was allowed to crystallize previously described. The yield of crystallized product from this second crop was 6 gm of an off-white crystalline solid. Therefore, the total yield of crystallized product from the above procedure was 38 gm (or 76% yield). Phosphorus NMR showed only one peak for the crystallized SPA product.

The foregoing Examples, since they only illustrate certain embodiments of the claimed invention, should not be construed in a limiting sense. The scope of protection sought is set forth in the claims which follow.

We claim:

1. A process for the formation of styrene phosphonic acid which comprises the reaction of phosphorous acid with acetophenone to form a hydroxy adduct intermediate thereof which is then reacted with acetic anhydride to form the acyl derivative of the hydroxy adduct, followed by removal of an acetic acid moiety therefrom to form the styrene phosphonic acid product.

2. A process as claimed in claim 1 wherein the hydroxy adduct intermediate has the formula

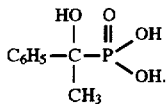

3. A process as claimed in claim 1 wherein the acyl derivative of the hydroxy adduct intermediate has the formula

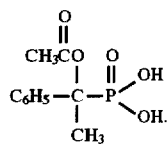

4. A process as claimed in claim 1 wherein the catalyzed reaction of phosphorous acid with acetophenone is conducted in the presence of a Lewis acid catalyst.

5. A process as claimed in claim 1 wherein the removal of an acetic acid moiety from the acyl derivative of the hydroxy adduct to form the styrene phosphonic acid product is conducted in the presence of an acidic catalyst.

6. A process as claimed in claim 2 wherein the catalyzed reaction of phosphorous acid with acetophenone is conducted in the presence of a Lewis acid catalyst and wherein the removal of an acetic acid moiety from the acyl derivative of the hydroxy adduct to form the styrene phosphonic acid product is conducted in the presence of an acidic catalyst.

7. A process as claimed in claim 3 wherein the catalyzed reaction of phosphorous acid with acetophenone is conducted in the presence of a Lewis acid catalyst and wherein the removal of an acetic acid moiety from the acyl derivative of the hydroxy adduct to form the styrene phosphonic acid product is conducted in the presence of an acidic catalyst.

* * * * *